US00PP21295P2

(12) United States Plant Patent
Korlipara

(10) Patent No.: US PP21,295 P2
(45) Date of Patent: Sep. 14, 2010

(54) ***AJUGA* PLANT NAMED 'SPARKLER'**

(50) Latin Name: ***Ajuga* sp.**
Varietal Denomination: Sparkler

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 12/586,209

(22) Filed: Sep. 17, 2009

(51) Int. Cl.
*A01H 5/00* (2006.01)

(52) U.S. Cl. ..... Plt./401

(58) Field of Classification Search ..... Plt./401
See application file for complete search history.

*Primary Examiner*—Annette H Para
(74) *Attorney, Agent, or Firm*—Klarquist Sparkman, LLP

(57) ABSTRACT

A new and distinct form of *Ajuga* plant characterized by vigor, white mottled variegation, and low creeping habit.

1 Drawing Sheet

Botanical denomination: *Ajuga* sp.
Variety designation: 'Sparkler'.

BACKGROUND OF THE INVENTION

The present invention relates to a new and distinct cultivar of *Ajuga*, given the name, 'Sparkler'. *Ajuga* is in the family Lamiaceae. This plant originated in the lab from a plant brought back from Japan labeled *Ajuga decumbens* White Mottled (an unpatented plant). *Ajuga* 'Sparkler' differs from its parent plant in being much more vigorous and less white mottled.

*Ajuga* 'Sparkler' is unique in its combination of vigor, white mottled variegation, purple violet new leaves, and low creeping habit. There are no similar plants in the commercial market known to the breeder.

The new variety has been reproduced only by asexual propagation (cuttings, division, and micropropagation). Each of the progeny exhibits identical characteristics to the original plant. Asexual propagation by cuttings, division, and micropropagation using terminal and lateral shoots as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a six month-old *Ajuga* 'Sparkler' growing in the trial beds in early August in Canby, Oreg.

FIG. 2 shows a close up of the same plant 8 months later in April in flower.

DETAILED PLANT DESCRIPTION

The following is a detailed description of the new *Ajuga* cultivar based on observations of one-year-old specimens grown outside in the ground in the trial beds in Canby, Oreg. The color descriptions are all based on The Royal Horticultural Society Colour Chart, 5$^{th}$ edition.

Plant:

*Form.*—Stoloniferous, herbaceous perennial.
*Cold hardiness.*—USDA Zone 4-9.

*Size.*—Grows to 35 cm wide and 10 cm high.
*Vigor.*—Excellent.
*Stem.*—Decumbent and rosette, rooting at each node, grows to 14 cm long and 5 mm wide, pubescent, Grey Brown 199D on last years growth and Yellow Green 146C tinted Greyed Purple 187B on new growth.
*Roots.*—Grey Brown 199D, thickened to fibrous, plants root easily from stem cuttings.

Leaf:

*Type.*—Simple, basal leaves longer than the stem leaves.
*Arrangement.*—Opposite and rosette.
*Shape.*—Spatulate and cupping.
*Venation.*—Pinnate.
*Margins.*—Irregularly coarsely dentate.
*Apex.*—Acute.
*Base.*—Attenuate.
*Blade size.*—Grows to 5 cm long and 1 cm wide.
*Surface texture.*—Pubescent on both sides.
*Leaf color.*—Top side spring leaves are Yellow Green 147A irregularly mottled with White 155A and Yellow Green 148D, bottom side Yellow Green 147B mottled with 148D and 155A; immature leaves White 155A tinted Purple Violet N81A; summer leaves topside are Yellow Green.

Inflorescence:

*Type.*—Terminal many flowered verticillasters, basally widely spaced, apically crowded in interrupted spikes.
*Number of flowers.*—One to five per spike.
*Size of inflorescence.*—4 cm long and 2.5 cm wide.
*Peduncle.*—4 cm long and 2 mm wide, pubescent, Greyed Brown 199B.
*Pedicel.*—1 to 2 mm long, Yellow Green 147D.
*Floral leaves.*—Subtending spikes, 4 cm long and 0.5 cm wide at base and 1 cm long and 4 mm wide on top of flowering stem, obovate to oblanceolate, acute, irregularly dentate, cupped, colored the same as the basal leaves.
*Bloom period.*—April to May in Canby, Oreg.

Flower bud:

*Size.*—5 mm long and 2 mm wide at the widest point prior to opening.
*Description.*—Ovoid.

*Surface texture.*—Pubescent.

*Color.*—Violet Blue 90A.

Flower:

*Type.*—Zygomorphic.

*Shape.*—Bilabiate.

*Corolla description.*—10 mm long and spreads to 4 mm wide, tube and throat 4 mm long and 1 mm wide, 2 small upper lobes triangular, less than 1 mm long and wide, acute, three lower lobes, 3 mm long, entire, acute, two on side narrowly triangular, the terminal lobe obovate, entire, glabrous inside, villous outside, color inside Violet Blue 90A, outside Violet Blue 90B.

*Calyx description.*—Funnel-form, 5 lobed, 4 mm long and 2 mm wide, lobes narrow 3 mm long acute, entire, strongly pubescent outside, glabrous inside, White NN155C with streaks of Yellow Green 147B.

*Pistil description.*—One, 7.5 mm long, ovary 0.5 mm long, Yellow Green 146C, style and stigma 7 mm long, Violet N88B.

*Stamen description.*—Four, 3 mm long filaments Violet N88C, anthers Black 202A, pollen Yellow 8D.

*Fragrance.*—None.

*Lastingness.*—A spike blooms for about 3 weeks on the plant.

Fruit and seed: Not seen.

Pests and diseases: *Ajuga* are known to be susceptible to southern blight and various fungal leaf spots, crown rot, and fungal root rot. The new cultivar has shown no problems in Canby, Oreg.

I claim:

1. A new and distinct form of *Ajuga* plant substantially as shown and described.

* * * * *

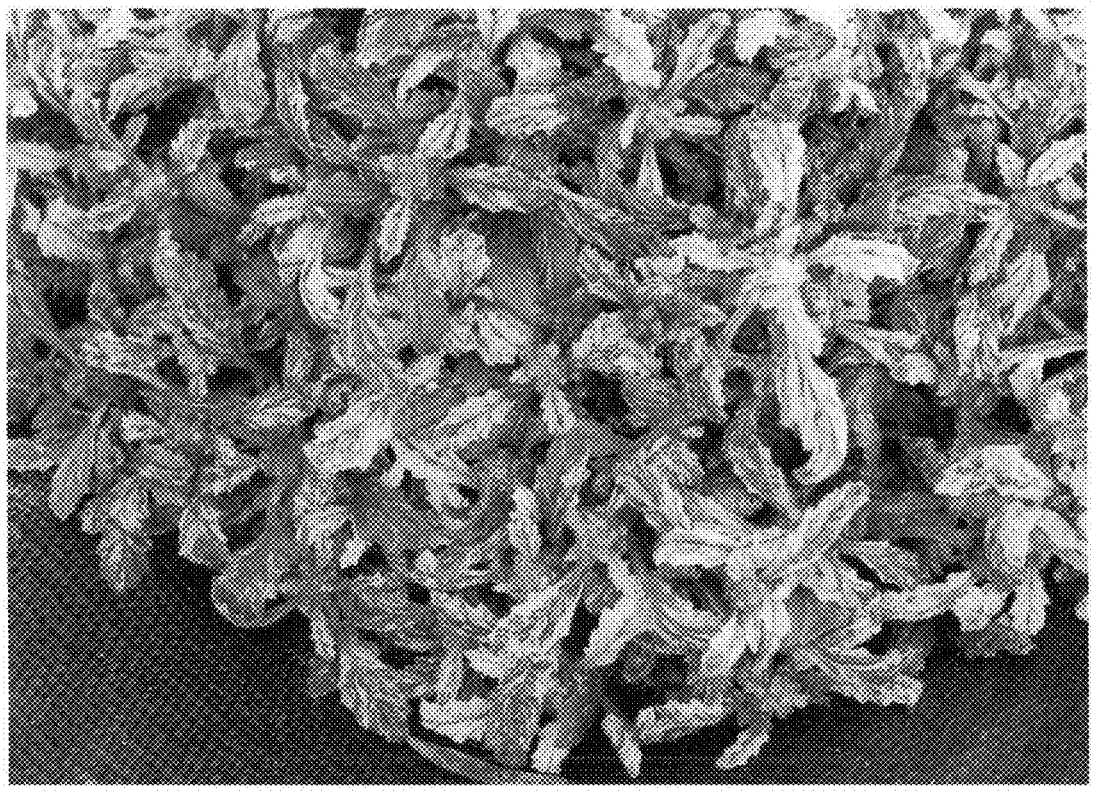

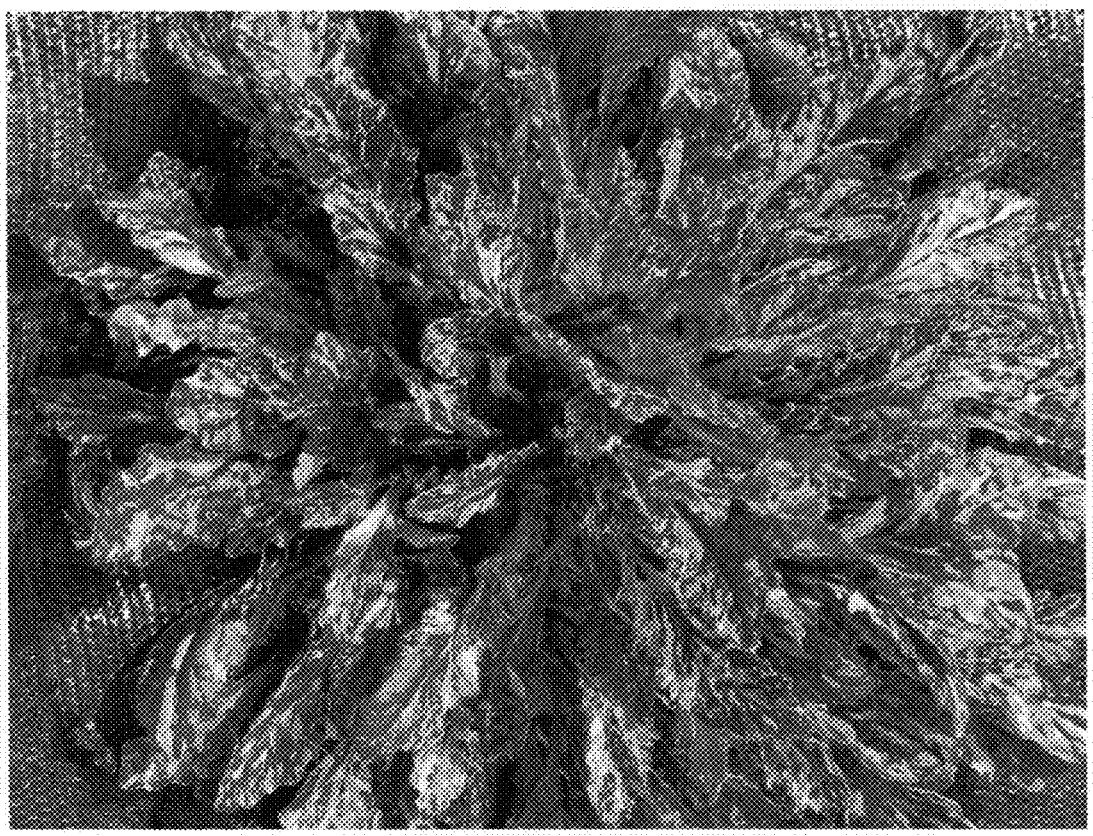
Figure 1 above, figure 2 below